(12) United States Patent
Li

(10) Patent No.: US 6,500,132 B1
(45) Date of Patent: Dec. 31, 2002

(54) DEVICE AND METHOD FOR DETERMINING PARAMETERS OF BLIND VOIDS

(75) Inventor: Lehmann K. Li, Milford, CT (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 09/894,727

(22) Filed: Jun. 28, 2001

Related U.S. Application Data

(60) Provisional application No. 60/215,486, filed on Jun. 30, 2000.

(51) Int. Cl.[7] ................................................ A61B 5/107
(52) U.S. Cl. ........................ 600/594; 33/512; 128/898
(58) Field of Search ................................ 600/594, 587; 33/511, 512; 128/898

(56) References Cited

U.S. PATENT DOCUMENTS 3,918,164 A * 11/1975 Krautmann ............... 33/511 X
5,197,465 A * 3/1993 Montgomery ............. 33/512 X
5,471,756 A * 12/1995 Bolanos et al. ........... 33/512 X
5,823,974 A * 10/1998 Grassi ..................... 600/594 X
6,224,599 B1 * 5/2001 Baynham et al. ............. 606/61

* cited by examiner

Primary Examiner—Kevin Lee
(74) Attorney, Agent, or Firm—Woodard, Emhardt, Naughton, Moriarty & McNett LLP

(57) ABSTRACT

Device for determining the size of a blind void comprises an elongated rigid rod, an actuator slidably movable relative to the rod, the actuator having a distal end for insertion into the void, a distal flexible element fixed at one end thereof to the rod, a second flexible element fixed at one end thereof to the rod and proximally removed from the distal flexible element. Movement of the actuator is operative to cause equal movements of the distal end portions of the distal and proximal elements, to cause the distal element to bulge outwardly from the rod to engage interior walls of the void and to cause the proximal element to bulge outwardly in a configuration duplicative of the distal element bulge, the proximal element being outside of the void and subject to observation.

22 Claims, 4 Drawing Sheets

DEVICE AND METHOD FOR DETERMINING PARAMETERS OF BLIND VOIDS

REFERENCE TO PENDING PRIOR PATENT APPLICATION

This patent application claims benefit of pending prior U.S. Provisional Patent Application Ser. No. 60/215,486, filed Jun. 30, 2000 by Lehmann K. Li for REMOTE MEASURING APPARATUS AND METHOD, which patent application is hereby incorporated herein by reference.

FIELD OF THE INVENTION

This invention relates to the field of surgical devices used primarily for the repair or replacement of human tissue, including, but not limited to, the nucleus pulposus of the spine. The invention further relates to the method of using such devices.

BACKGROUND OF THE INVENTION

The spinal column is a flexible chain of closely linked vertebral bodies. In a normal human spine there are seven cervical, twelve thoracic and five lumbar vertebral bodies. Below the lumbar vertebrae are the sacrum and coccyx. Each individual vertebra has an outer shell of hard, dense bone. Inside the vertebra is a honeycomb of cancellous bone containing red bone marrow. All of the red blood cells and many of the white blood cells are generated inside this cancellous bone, where the blood cells mature before being released into the blood circulation.

The spinal disc serves as a cushion between the vertebral bodies to permit controlled motion. A healthy disc consists of three components: a gelatinous inner core called the nucleus pulposus; a series of overlapping and laminated plies of tough fibrous rings called the annulus fibrosus; and two superior and inferior thin cartilage layers, connecting the disc to the thin cortical bone of the vertebral bodies, called the endplates.

The spinal disc may be displaced or damaged due to trauma or disease, such as a herniation or degenerative disc disease.

A herniated disc may bulge out and compress itself onto a nerve, resulting in lower leg pain, loss of muscle control, or paralysis. To treat a herniated disc, the offending nucleus portions are generally removed surgically.

Disc degeneration gradually reduces disc height, forcing the annulus to buckle, tear or separate radially or circumferentially, and causing persistent and disabling back pain. Degenerative disc disease is generally treated presently by surgically removing the nucleus and fusing the adjacent vertebral bodies to stabilize the joint.

In either case, whether removing a portion of the nucleus or all of the nucleus, these procedures ultimately place greater stress on adjacent discs to compensate for the lack of motion, which may cause premature degeneration of those adjacent discs.

Modern trends in surgery include the restoration of bodily function and form (i.e., repair) of anatomical structures through the use of minimally invasive surgical techniques. The ability to surgically repair damaged tissues or joints, creating as few and as small incisions as possible, produces less trauma, less pain and better clinical outcomes in general.

An emerging technique to treat degenerative disc disease is to replace the degenerated nucleus with a prosthetic nucleus in an attempt to restore function, versus fusion which severely limits the function of the spine. Since a degenerated nucleus can be removed using relatively small diameter instruments (e.g. 5 mm or less), this approach is more conducive to minimally invasive techniques.

A deficiency of current minimally invasive surgical techniques to replace the nucleus is the difficulty in determining whether enough space in the disc has been created to properly fit an implant. Creating the proper dimension cavity may be particularly important when implanting a device that expands, such as with a hydrogel implant. If the cavity created is larger than the implant, unintended implant movement or instability can occur. If the cavity created is smaller than the implant, an implant either may not fit, may not be positioned correctly or an expandable device may not achieve its proper functional shape.

SUMMARY OF THE INVENTION

It is, therefore, one object of the present invention to provide a device and method for determining how much space is created in human tissue, particularly when the space is in a visually impaired location.

A further object of the invention is to provide a device and method for determining how much space is created in the inner portion of the intervertebral disc space to facilitate the implantation of an artificial nucleus pulposus. The present invention is adapted to be placed through a small opening created in the annulus to minimize trauma to surrounding tissue.

With the above and other objects in view, a feature of the invention is the provision of a device for determining parameters of a blind void. The device comprises an elongated rigid rod, and an actuator extending lengthwise of the rod and slidably movable relative to the rod, the actuator having a distal end for insertion into the void. A first flexible element is fixed at one end thereof to the rod proximate the distal end of the rod. A second flexible element is fixed at one end thereof to the rod and proximally removed from the distal end of the rod and from the first element. Movement of the actuator is operative to cause equal movements of the distal end portions of the first and second elements, to cause the first element to bulge outwardly from the rod to engage interior walls of the void and to cause the second element to bulge outwardly in a configuration substantially duplicative of the first element bulge, the second element being outside of the void and subject to observation.

In accordance with a further feature of the invention, there is provided a method for determining parameters of a blind void, the method comprising the steps of providing a device comprising an elongated rigid rod, a first flexible element fixed at one end thereof to the rod proximate a distal end of the rod, a second flexible element fixed at one end thereof to the rod and proximally removed from the distal end of the rod and from the first element, and an actuator extending lengthwise of the rod and engageable with distal end portions of the first and second elements. The method further includes the steps of inserting the distal end of the actuator and the first element into the void, moving the actuator to cause movements of the distal end portions of the first and second elements, to cause the first element to bulge outwardly to engage interior walls of the void, and to cause the second element to bulge outwardly in a configuration duplicative of the first element bulge, the second element being outside of the void, and determining from the size of the second element the size of the first element and thereby the void.

The above and other features of the invention, including various novel details of construction and combinations of parts and method steps, will now be more particularly described with reference to the accompanying drawings and pointed out in the claims. It will be understood that the particular device and method embodying the invention are described by way of illustration only and not as limitations of the invention. The principles and features of this invention may be employed in various and numerous embodiments without departing from the scope of the invention.

BRIEF DESCRIPTION OF THE DRAWINGS

Reference is made to the accompanying drawings in which is shown an illustrative embodiment of the invention, from which its novel features and advantages will be apparent.

In the drawings.

DETAILED DESCRIPTION OF THE PREFERRED EMBODIMENTS

Figure 1:
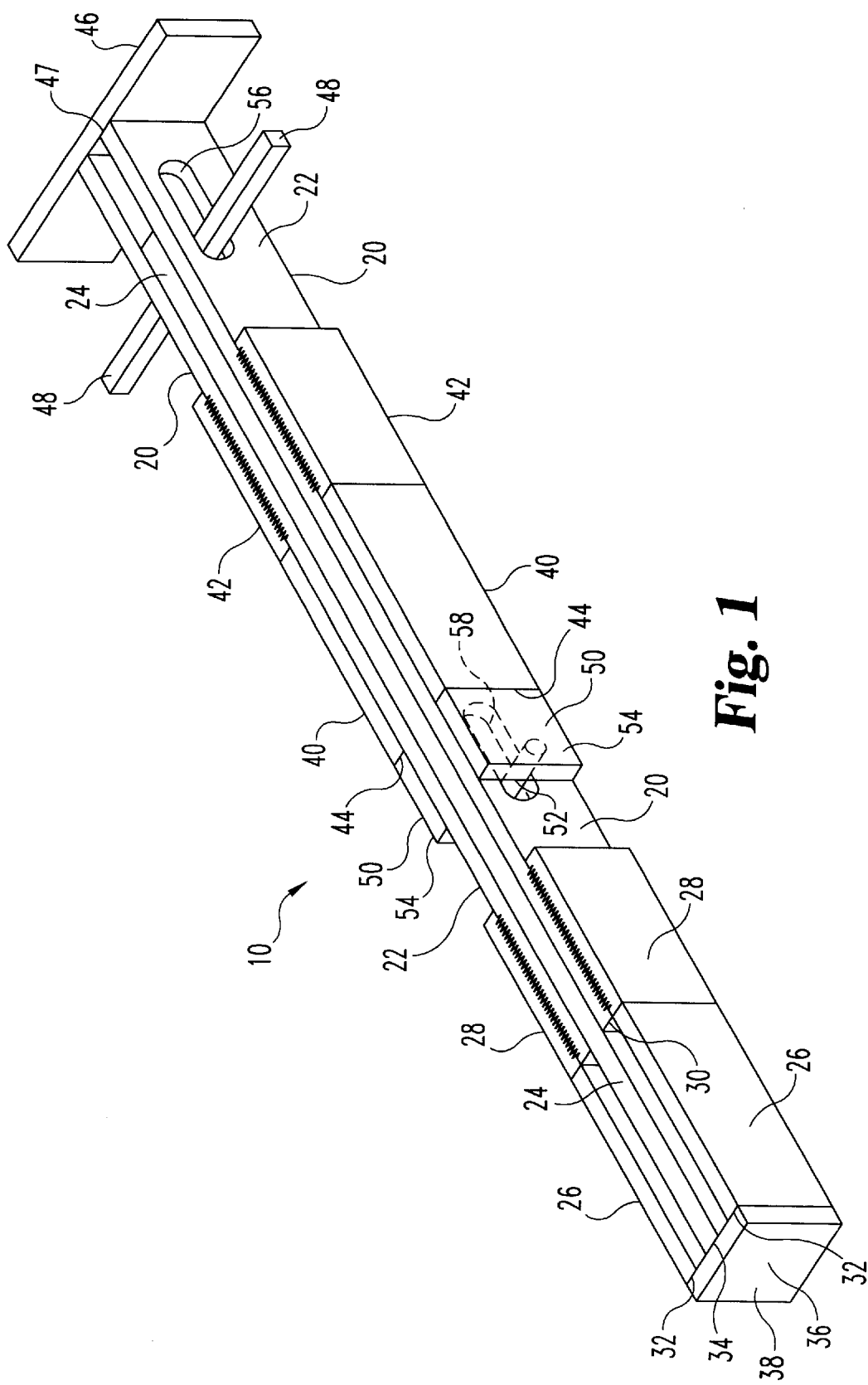
FIG. 1 is a perspective view of one form of device illustrative of an embodiment of the invention.

Referring to FIG. 1, it will be seen that an illustrative inventive device 10 includes an elongated rigid rod 20, in the form of at least one, and preferably two, plates 22. When the device includes two plates, the plates extend parallel to each other.

An actuator 24 extends lengthwise of the rod 20 and is slidably movable relative to the rod 20. When the rod 20 includes two plates 22, the actuator 24 is slidably disposed between the two plates.

A first flexible element, such as a strip 26, is fixed at a proximal end portion 28 thereof to the rod 20 proximate the distal end 30 of the rod. The element 26 may be a bendable strip of metal having a distal free end 32. A first flexible element 26 is fixed to each of the plates 22.

Mounted on a distal end 34 of the actuator 24 is a first engagement member 36 which is engageable with the distal end 32 of each of the first elements 26. The first engagement member 36 may be an end-piece 38 fixed to the distal end 34 of the actuator 24.

A second flexible element, such as a strip 40, is fixed to each of the plates 22 at a proximal end portion 42 of the element. The element 40 is of the same configuration, size and material as the element 26 and is provided with a distal free end 44. A flexible second element 40 is fixed to each of the plates 22 proximally of the distal end 30 of the rod 20 and proximally of the first flexible element 26.

Mounted on each of the plates 22 on a side opposite from the actuator 24 is a second engagement member 50 connected to the actuator 24 by a connecting pin 52. The second engagement member 50 may be a block 54.

The rod 20 is provided with a grip portion 46 at the proximal end 47 of the rod by which the rod may be gripped by an operator (not shown). The actuator 24 is provided with a manipulable portion, such as a cross-bar 48, such that an operator may hold the device 10 in one hand by gripping the rod grip portion 46 and the actuator cross-bar 48, and by squeezing the cross-bar toward the grip portion, cause the actuator to move proximally relative to the plates 22. The plates are each provided with a slot 56 through which extends a cross-bar portion, such that the cross-bar 48 may readily move relative to plates 22. Similarly, the plates 22 are each provided with a slot 58 through which extends the connecting pin 52, permitting movement of the engagement block 54 relative to the plates 22.

Figure 2:
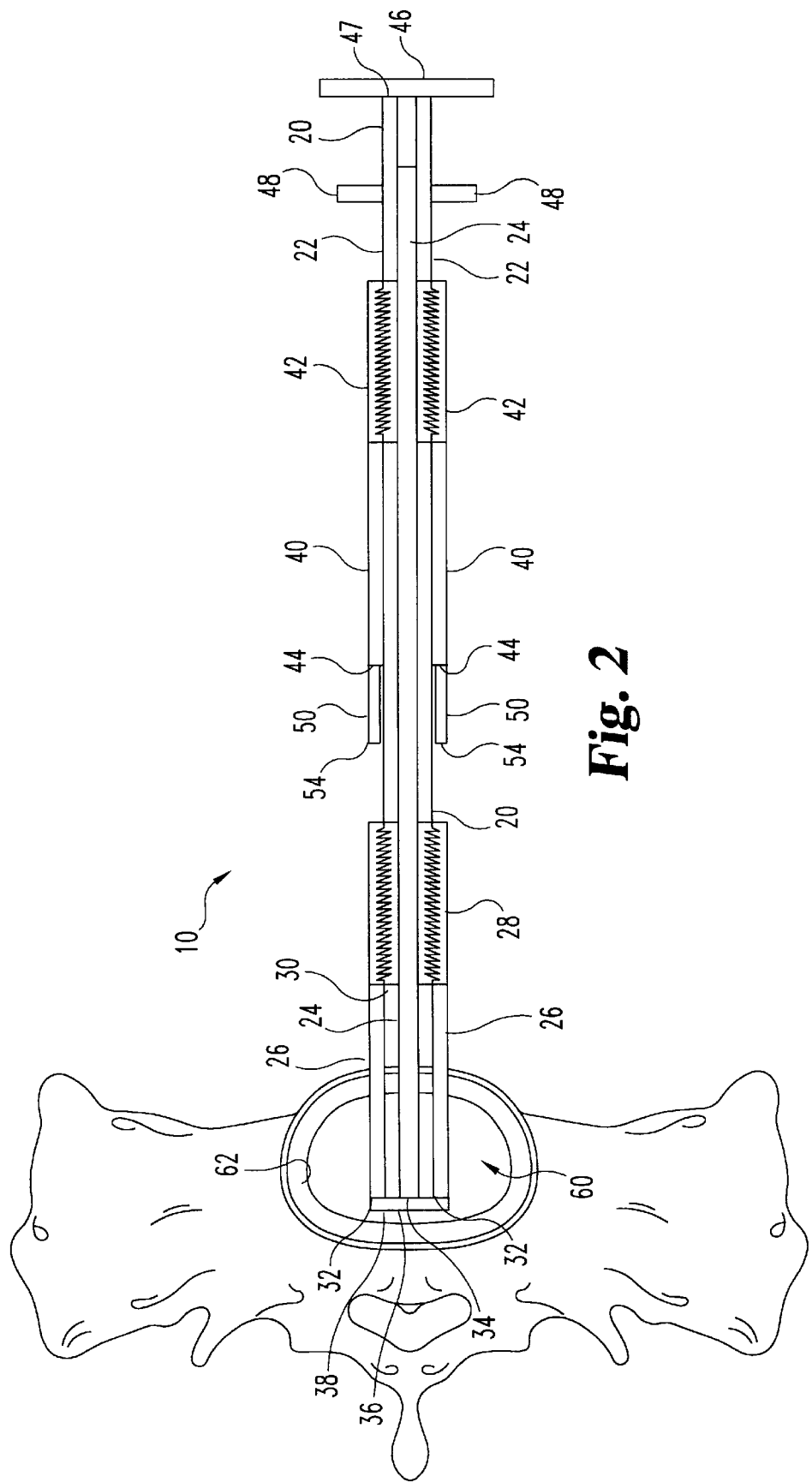
FIG. 2 is a diagrammatic top view of the device of FIG. 1 deployed in a spinal disc.
Figure 3:
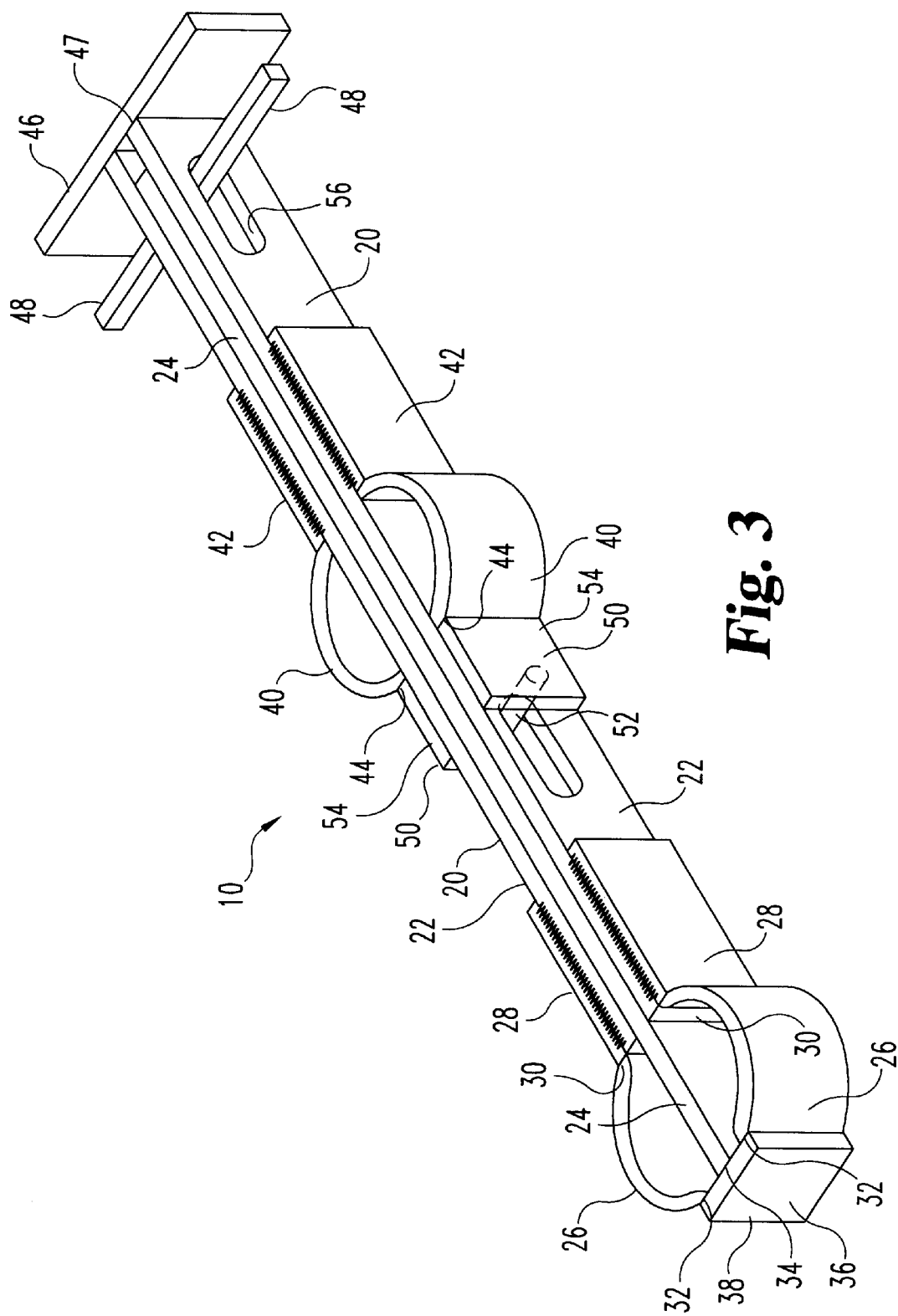
FIG. 3 is similar to FIG. 1, but shows the device in another operative configuration.
Figure 4:
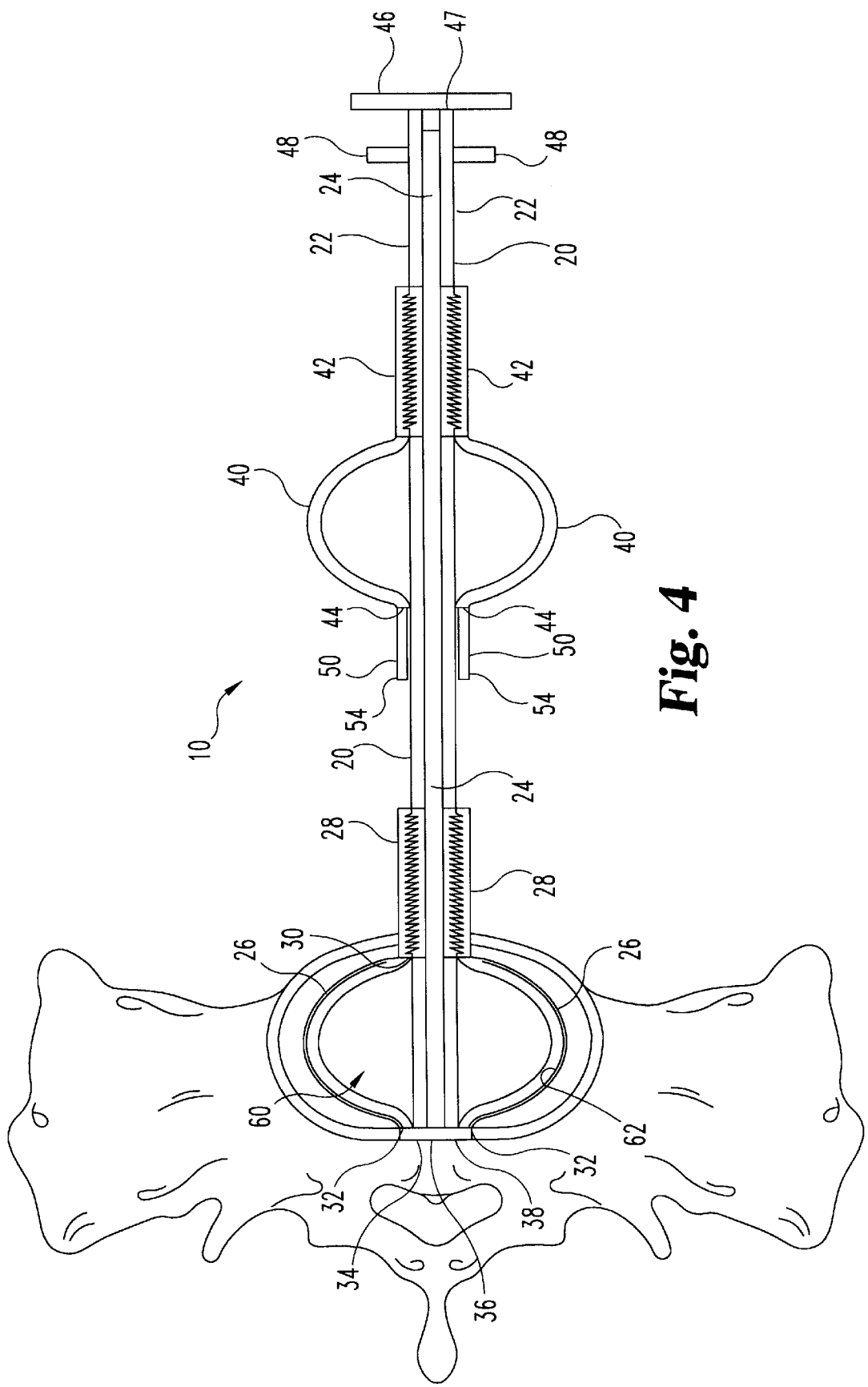
FIG. 4 is similar to FIG. 2, but shows the device in a parameter determining configuration.

In operation, the device 10, as shown in FIG. 1, is inserted into a void, such as a spinal disc cavity 60 from which the nucleus pulposus has been removed (FIG. 2). By manipulation of the rod grip portion 46 and actuator cross-bar 48, the actuator 24 is made to move proximally relative to the rod 20. Proximal movement of the actuator 24 carries with it proximal movement of the end piece 38 and engagement block 54 which, contacting the element free distal ends 32,44, respectively, cause proximal movement of the flexible element free ends 32,44, while the flexible element proximal ends 28,42 remain fast to their respective plates 22. The elements are thus caused to bulge outwardly (FIGS. 3 and 4) until the first element 26 engages interior walls 62 of the cavity 60, stopping movement of the actuator 24.

At this point, the first element 26 is hidden from view and the extent of the bulge is not ordinarily observable. However, because the second flexible element 40 is of the same configuration, size and material as the first element and expands in a manner duplicating the expansion of the first element, and is in an observable disposition, the size of the spinal disc cavity may be determined by observation of the second element. While it is intended that "observation" includes visual observation and mechanical measurement, it is apparent that "observation" can be undertaken by optical or automatic data gathering instruments in combination with computers and/or read-out devices.

It should also be appreciated that device 10 may be used to determine cavity sizes in a variety of different directions. Thus, for example, in FIGS. 2–4, device 10 is shown oriented so as to measure cavity size in a substantially horizontal direction. However, it should also be appreciated that device 10 may be oriented, or modified, so as to measure cavity size in a substantially vertical direction, or in some other direction.

There is thus provided a device and method for determining the space available in a blind void, and particularly in a spinal disc cavity vacated by extraction of the nucleus pulposus therefrom.

It is to be understood that the present invention is by no means limited to the particular construction herein disclosed and/or shown in the drawings, but also comprises any modification or equivalent within the scope of the claims.

What is claimed is:

1. A device for determining parameters of a blind void, the device comprising:

an elongated rigid rod;

an actuator extending lengthwise of said rod and slidably movable relative to said rod, said actuator having a distal end for insertion into the void;

a first flexible element fixed at one end thereof to said rod proximate the distal end of said rod;

a second flexible element fixed at one end thereof to said rod and proximally removed from the distal end of said rod and from said first element;

wherein movement of said actuator is operative to cause equal movements of the distal end portions of said first and second elements, to cause said first element to bulge outwardly from said rod to engage interior walls of the void and to cause said second element to bulge outwardly in a configuration duplicative of said first element bulge, the second element being outside of the void and subject to observation.

2. The device in accordance with claim 1 wherein said actuator is engageable with distal end portions of said first and second elements to cause the movements of said distal end portions of said elements and thereby the bulging outwardly of said elements.

3. The device in accordance with claim 1 wherein said actuator comprises an end piece fixed to the distal end of said actuator and engageable with a distal end of said first flexible element, and a projection engageable with a distal end of said second flexible element, such that the distal ends of the elements are moved toward the fixed ends of the elements to cause portions of the elements between the distal and fixed ends thereof to bulge outwardly.

4. The device in accordance with claim 1 wherein said rod is provided with a grip portion at a proximal end thereof and said actuator is provided with a manipulable portion proximate a proximal end of said actuator and proximate the grip portion.

5. The device in accordance with claim 1 wherein said elements each comprise at least one strip of flexible material.

6. The device in accordance with claim 1 wherein said actuator comprises a rigid elongated member.

7. A device for determining parameters of a blind void, the device comprising:
  an elongated rod having a proximal end and a distal end;
  an actuator slidably mounted on said rod for movement distally and proximally on said rod;
  first and second flexible elements fixed to a surface of said rod opposite from said actuator, said first flexible element being disposed at a distal end of said rod and said second flexible element being disposed proximally of said first element, said elements being substantially identical to each other;
  first and second engagement members fixed to said actuator and engageable with distal ends of said first and second elements, respectively;
  wherein proximal movement of said actuator relative to said rod causes said engagement members to contact the distal ends of said elements to bulge said elements outwardly to produce first and second identical bulges, one of the bulges being exposed for observation.

8. The device in accordance with claim 7 wherein said rod comprises first and second plates of equal configuration and size and extending parallel to each other, and said actuator is slidably disposed between said first and second plates, each of said plates having the first and second flexible elements fixed thereon on outwardly facing walls thereof, and the engagement members engage the distal ends of all of said flexible elements to cause bulging of all of said elements simultaneously.

9. The device in accordance with claim 8 wherein said rod is provided with a grip portion at a proximal end thereof and said actuator is provided with a manipulable portion proximate the grip portion, such that an operator can hold said rod and move said actuator with one hand.

10. A device for determining the size of a spinal disc void created by removal of nucleus pulposus, such that an artificial nucleus implant may be properly sized before attempted implantation thereof, the device comprising:
  an elongated rod;
  an actuator extending lengthwise of said rod and slidably movable relative to said rod, said actuator having a distal end for insertion into the disc void;
  a first flexible element fixed at one end to said rod proximate a distal end of said rod for insertion into the disc void;
  a second flexible element fixed at one end to said rod and removed from said first element and the distal end of said rod to remain outside of the disc void; and
  engagement members mounted on said actuator, each engagement member upon movement of said actuator, being engageable with a free end of one of said elements to bulge outwardly said first element in the disc void and to bulge outwardly said second element to the same extent as the first element, such that the bulge of the second element is available to inspection and replicates the bulge of said first element.

11. The device in accordance with claim 10 wherein said engagement members comprise an end piece fixed to a distal end of said actuator and a block fixed to a side of said actuator, said end piece being engageable with the free end of said first element to cause said first element to bulge outwardly in the disc void, and said block being engageable with the free end of said second element to cause said second element to bulge outwardly.

12. The device in accordance with claim 11 wherein said rod comprises first and second plates extending parallel to each other, and said actuator comprises a plate slidably disposed between the rod first and second plates.

13. The device in accordance with claim 11 wherein said rod comprises two parallel plates and said actuator is disposed between said plates, said first flexible element being fixed on an outwardly facing surface of a first of the plates, another first flexible element being fixed on an outwardly facing surface of a second of the plates, said end piece being engageable with the free ends of both first elements simultaneously, said second flexible element being fixed on an outwardly facing surface of the first of the plates, another second flexible element being fixed on an outwardly facing surface of the second of the plates, said block being disposed on an outwardly facing surface of the first plate, and another block being disposed on an outwardly facing surface of the second of the plates.

14. The device in accordance with claim 13 wherein said blocks are fixed to said actuator by connecting pins which extend through slots in the plates.

15. The device in accordance with claim 13 wherein said rod includes a grip portion at a proximal end of said rod, and said actuator includes manipulation structure proximate the grip portion, such that the device is adapted to be held and operated by one hand of an operator.

16. The device in accordance with claim 15 wherein the manipulation structure comprises a cross-bar extending width-wise of said said actuator and through slots in the plates.

17. A method for determining parameters of a blind void, the method comprising the steps of:
  providing a device comprising:
    an elongated rigid rod;
    a first flexible element fixed at one end thereof to said rod proximate a distal end of said rod;
    a second flexible element fixed at one end thereof to said rod and proximally removed from the distal end of said rod and from said first element; and
    an acutator extending lengthwise of said rod and engageable with distal end portions of said first and second elements;
  inserting the distal end of said actuator and said first element into the void;
  moving said actuator to cause movements of the distal end portions of said first and second elements, to cause said first element to bulge outwardly to engage interior walls of the void, and to cause said second element to bulge outwardly in a configuration duplicative of the first element bulge, the second element being outside of the void; and determining from the size of the second element the size of the first element and thereby the void.

18. The method in accordance with claim 17 wherein:

said device includes a grip portion disposed at a proximal end of said rod, and a manipulable portion disposed on said actuator; and the step of moving said actuator comprises squeezing the grip portion towards the manipulative portion.

19. A method for determining the size of a spinal disc void created by removal of nucleus pulposus, such that an artificial nucleus implant may be properly sized before attempted implantation thereof, the method comprising the steps of:

providing a device comprising:
first and second plates disposed side by side and parallel to each other;
a distal flexible element fixed at one end thereof to each of said plates;
a proximal flexible element fixed at one end thereof to each of said plates, said proximal elements being proximally removed from said distal elements; and
an actuator extending slidably between said plates and having portions thereof engageable with free distal end portions of said flexible elements;

inserting a distal end of said actuator and said distal elements into the spinal disc void;

moving said actuator to cause the actuator engageable portions to engage the free distal end portions of said elements to cause said distal elements to bulge outwardly to engage interior walls of the void and to cause said proximal elements to bulge outwardly in a configuration duplicative of the distal elements' bulges, the proximal elements being outside of the void; and observing the size of the bulged proximal elements to determine the size of the bulged distal elements, and thereby the size of the void.

20. The method in accordance with claim 19 wherein observing the bulged proximal elements includes at least one of visual observation and automatic data gathering and read-out.

21. The method in accordance with claim 19 wherein said actuator is oriented so as to determine the size of the void in a substantially horizontal direction.

22. The method in accordance with claim 19 wherein said actuator is oriented so as to determine the size of the void in a substantially vertical direction.

* * * * *